US009045783B2

(12) United States Patent
Marshall et al.

(10) Patent No.: US 9,045,783 B2
(45) Date of Patent: *Jun. 2, 2015

(54) PROCESS FOR THE PRODUCTION OF OPTICALLY-ACTIVE ESTERS OF LACTIC ACID AND LACTYLLACTIC ACID

(75) Inventors: Edward Leslie Marshall, London (GB); Jade Jocelyn Afriye Osei-Tutu, London (GB); Stephen Alexander Calder Smith, London (GB)

(73) Assignee: Plaxica Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/232,426

(22) PCT Filed: Jul. 16, 2012

(86) PCT No.: PCT/GB2012/051696
§ 371 (c)(1),
(2), (4) Date: Apr. 9, 2014

(87) PCT Pub. No.: WO2013/011296
PCT Pub. Date: Jan. 24, 2013

(65) Prior Publication Data
US 2014/0342413 A1 Nov. 20, 2014

(30) Foreign Application Priority Data

Jul. 15, 2011 (GB) .................... 1112296.7
Jul. 15, 2011 (GB) .................... 1112297.5
Jun. 11, 2012 (GB) .................... 1210275.2

(51) Int. Cl.
*C12P 33/04* (2006.01)
*C12P 7/62* (2006.01)
*C12P 41/00* (2006.01)
*C12P 7/56* (2006.01)
*C12P 17/06* (2006.01)

(52) U.S. Cl.
CPC ............... *C12P 7/62* (2013.01); *C12P 41/003* (2013.01); *C12P 7/56* (2013.01); *C12P 17/06* (2013.01)

(58) Field of Classification Search
USPC .................................. 435/139, 135
See application file for complete search history.

(56) References Cited

U.S. PATENT DOCUMENTS

| 2,371,281 | A | | 3/1945 | Claborn |
| 4,835,293 | A | * | 5/1989 | Bhatia ............................ 549/274 |
| 5,274,127 | A | * | 12/1993 | Sinclair et al. ................. 549/274 |
| 6,277,951 | B1 | | 8/2001 | Gruber et al. |
| 7,829,740 | B2 | | 11/2010 | Enomoto et al. |

FOREIGN PATENT DOCUMENTS

| CA | 2734102 A1 | 3/2010 |
| EP | 0657447 A | 6/1995 |
| GB | 2484674 A | 4/2012 |
| JP | 2009195149 A | 9/2009 |
| KR | 20050103691 A | 4/2004 |
| KR | 10-0592794 | 6/2006 |
| WO | 2004/081220 | 9/2004 |
| WO | 2010/005235 A2 | 1/2010 |
| WO | 2010/105142 A1 | 9/2010 |

OTHER PUBLICATIONS

Emel'yanenko et al, "The Thermodynamic Properties of S-Lactic Acid", Russian Journal of Physical Chemistry A, 2919, 84, No. 9, p. 1491-1497.
Findrik et al, "Evaluation of factors influencing the enantioselective enzymatic esterification of lactic acid in ionic liquid" Bioprocess Biosyst Eng., 2012, 35, p. 625-635.
Groot and Boren, "Life cycle assessment of the manufacture of lactide and PLA biopolymers from sugarcane in Thailand", Int J Life Cycle Assess, 2010, 15, p. 970-984.
Idris and Bukhari, "Immobilized *Candida antarctica* lipase B: Hydration, stripping off and application in ring opening polyester synthesis", Biotechnology Advances, 2012, 30, p. 550-556.
Jeon et al, "Synthesis of alkyl (R)-lactates and alkyl (S,S)-O-lactyllactates by alcoholysis of rac-lactide using Novozym 435" Tetrahedron Letters, 2006, 47, p. 6517-6520.
Jeon et al, "Lipase-catalysed enantioselective synthesis of R-lactide from alkyl lactate to produce PDLA (poly D-lactic acid) and stereocomplex PLA (poly lactic acid)", American Chemical Society, 241st ACS National Meeting, Mar. 27-31, 2011, p. 260-261 (Abstract).

(Continued)

*Primary Examiner* — Ralph Gitomer
(74) *Attorney, Agent, or Firm* — Kramer Levin Naftalis & Frankel LLP

(57) ABSTRACT

A process for treating a mixture of R,R- and S,S-lactide is provided. The process involves contacting the lactide mixture with an aliphatic alcohol and/or an alkoxide to produce a mixture of R,R- and S,S-aliphatic ester of lactyllactic acid, subsequently contacting the mixture of R,R- and S,S-aliphatic ester of lactyllactic acid with an enzyme to produce a mixture comprising aliphatic ester of lactic acid corresponding to one lactide enantiomer and the aliphatic ester of lactyllactic acid corresponding to the other lactide enantiomer, and recovering the product. Also provided are processes for the production of S-lactic acid, S,S-lactide, poly-S-lactic acid, R-lactic acid, R,R-lactide, poly-R-lactic acid and stereocomplex polylactic acid.

20 Claims, No Drawings

(56) References Cited

OTHER PUBLICATIONS

Jeon et al, "Improved catalysis of *Candida antarctica* lipase B (CALB) through protein engineering for conversion of Rlactide from alkyl R-lactate in organic solvent", The Korean Society for Biotechnology and Bioengineering, 2011 Spring Meeting, Apr. 14-16, 2011, p. 22.

Kazlauskas et al, "A Rule to Predict Which Enantiomer of a Secondary Alcohol Reacts Faster in Reactions Catalyzed by Cholesterol Esterase, Lipase from *Pseudomonas cepacia*, and Lipase from *Candida rugosa*", J. Org. Chem., 1991. 56, p. 2656-2665.

Lee et al, "Highly Enantioseslective Acylation of rac-Alkyl Lactates Using *Candida antarctica* Lipase B", Organic Process Research and Development, 2004, 8, p. 948-951.

Lunt, "Large-scale production, properties and commercial applications of polylactic acid polymers", Polymer Degradation and Stability, 1998, 59, p. 145-152.

Matsumoto et al, "Enzymatic and whole-cell synthesis of lactate-containing polyesters: toward the complete biological polyesters: toward the complete biological production of polylactate", Appl. Microbiol. Biotechnol., 2010, 85, p. 921-932.

Nemeth et al, "Asymmetric Lactic Acid Esterification with Biocatalysts in Ionic Liquid", Hungarian Journal of Industrial Chemistry, 2011, 39, p. 419-425.

Numata et al, "Branched Poly(lactide) Synthesized by Enzymatic Polymerization: Effects of Molecular Branches and Stereochemistry on Enzymatic Degradation and Alkaline Hydrolysis", Biomacromolecules, 2007, 8, p. 3115-3125.

Ohara et al, "Optical resolution of n-butyl D- and L-lactates using immobilized lipase catalyst", Journal of Bioscience and Bioengineering, 2011, 111, p. 19-21.

Shuklov et al, "Studies on the epimerization of diastereomeric lactides", Tetrahedron. Letters, 2011, 52, p. 1027-1030.

Smith and Claborn, "Lactic Esters Preparation and Properties", Industrial and Engineering Chemistry, 1940, 32, No. 5, p. 692-694.

Takwa et al, "Rational redesign of *Candida antarctica* lipase B for the ring opening polymerization of D,D-lactide", Chem. Commun., 2011, 47, p. 7392-7394.

Takwa, Lipase Specificity and Selectivity, Doctoral Thesis, Royal Institute of Technology, School of Biotechnology, Department of Biochemistry, Stockholm, Sweden, 2010.

Tsukegi et al, "Racemization behavior of L,L-lactide during heating", Polymer Degradation and Stability, 2007, 92, p. 552-559.

Yang and Liu, "Improved preparation of D, L-lactide from D, L-lactic acid using microwave irradiation", Polymer Bulletin, 2008, 61, p. 177-188.

\* cited by examiner

PROCESS FOR THE PRODUCTION OF OPTICALLY-ACTIVE ESTERS OF LACTIC ACID AND LACTYLLACTIC ACID

This application is the U.S. national phase filing of the corresponding international application number PCT/GB2012/051696, filed on Jul. 16, 2012, which claims priority to and benefit of GB Application No. 1112297.5, filed Jul. 15, 2011; GB Application No. 1112296.7, filed Jul. 15, 2011; and GB Application No. 1210275.2, filed Jun. 11, 2012 which applications are hereby incorporated by reference in their entirety.

The present invention relates to the production of single enantiomers of lactic acid, the cyclic dimer thereof (lactide) or lactate esters. In particular, it relates to a separation process in which a mixture of R,R- and S,S-lactide is alcoholised and the resulting mixture of R,R- and S,S-alkyl lactyllactate ester is then stereoselectively alcoholised in the presence of an enzyme to produce single enantiomers of different lactic acid derivatives which can then be easily separated.

Lactic acid (2-hydroxypropanoic acid) and its cyclic dimer lactide (3,6-dimethyl-1,4-dioxan-2,5-dione) are becoming increasingly important as building blocks for the chemical and pharmaceutical industries. An example of this is in the use of lactide to manufacture polylactic acid; a polymer whose ability to be produced from a variety of renewable feedstocks and biodegradability makes it an attractive candidate to replace more conventional petrochemical polymers, such as polyethylene terephthalate, for example in the fabrication of food and beverage containers. Today, lactide is made from lactic acid which in turn is typically made by the bacterial fermentation of monosaccharides derived from crops such as maize and other natural products. Lactic acid is chiral and can be made in two enantiomeric forms (respectively L-lactic acid (also referred to as S-lactic acid) on the one hand and D-lactic acid (R-lactic acid) on the other). Derivatives such as lactide are also chiral; lactide in particular exists in two enantiomeric forms (S,S-lactide and R,R-lactide) and a third diastereomeric R,S form sometimes also referred to as meso-lactide. The conventional fermentation technologies referred to above principally generate L-lactic acid with little D-lactic acid being formed. Although these technologies can be modified using different, often genetically engineered, bacteria to produce D-lactic acid in a similarly selective manner, to date the modified bacteria and the associated processes are expensive and difficult to use reliably on a large industrial scale. This is evidenced in the comparatively higher price and limited availability of D-lactic acid.

Polylactic acid is typically prepared in two steps in which lactic acid is first dehydrated to produce lactide and then the lactide is polymerised under carefully controlled conditions to ensure that long polymer chains are produced in preference to shorter oligomers. Since, as explained above, the most readily available source of lactic acid is L-lactic acid, the lactide employed commercially to date has been S,S-lactide and the polymer produced poly-L-lactic acid (PLLA) (also known as poly-S-lactic acid). However the physical properties of PLLA are limited relative to conventional polymers (as are those of the corresponding poly-D-lactic acid (PDLA), also known as poly-R-lactic acid) which to date has limited its utility.

It has been found that these deficiencies can be overcome by using mixtures of PLLA and PDLA which are prepared by, for example, melt blending. It is believed that in these so-called 'stereocomplex' polymer mixtures close packing of the PLLA and PDLA chains occasioned by their differing chirality improves polymer crystallinity which leads to improvements in the properties referred to above. This permits the use of stereocomplex PLA for a much wider range of consumer durable applications, making it a viable alternative with traditional commodity polymers such as polyethylene terephthalate, polypropylene and polystyrene. This approach however requires access to large quantities of PDLA and therefore ultimately to large quantities of D-lactic acid.

In addition to the use of fermentation methods, it is known to produce lactic acid by a conventional chemical transformation. For example, the prior art teaches it can be made by treating monosaccharides derived from a wide range of biological material with aqueous strong base. Such processes however are not stereoselective and generate a racemic mixture of the two enantiomers in approximately equal amounts. They are therefore attractive as a way of making the precursors of stereocomplex polylactic acid. There is a problem however with using racemic lactic acid to make polylactic acid in that the resulting polymer is amorphous and therefore also has poor processing properties. It is therefore necessary to separate the enantiomers present in the racemic lactic acid or those in the corresponding racemic lactide so that the enantiomers of the latter can be polymerised separately and the two chiral polymers mixed only at the final formulation stage.

Separating a racemic mixture into its constituent enantiomers is in general terms a well-known endeavor and strategies adopted have included fractional crystallisation and chromatography. However neither of these methodologies is easy to operate on a large scale, especially in commodity scale polymer manufacturing where throughputs are high and operating costs need to be carefully controlled. What is needed therefore is a simple chemical engineering solution which can be easily and reproducibly operated at scale.

Jeon et al in Tetrahedron Letters 47 (2006) 6517-6520 disclose the laboratory observation that racemic lactide can be alcoholised with various alcohols in the presence of a solvent and the supported lipase enzyme Novozym 435 to produce a product comprising a mixture of the corresponding R-alkyl lactate and the S,S alkyl lactyllactate. However, this reference goes no further than describing the chemistry.

We have now found that the process described in Jeon et al can be significantly improved if it is carried out in two stages which comprise first ring-opening the lactide enantiomers in the presence of an aliphatic alcohol to produce a racemic mixture of R,R- and S,S-aliphatic lactyllactate esters and then treating the racemic mixture so formed with the enzyme to generate an aliphatic ester of lactic acid corresponding to one lactide enantiomer, and the aliphatic ester of lactyllactic acid corresponding to the other lactide enantiomer. Thereafter the two products can be recovered, preferably they may be separated by distillation.

Once these two components are separated, the fact that they are associated with different enantiomers of lactic acid means that by subsequent chemical transformations they can each be converted to optically pure R,R- and S,S-lactide, or if desired optically pure R- and S-lactic acid which can be used in non-polymer producing applications.

According to the present invention there is therefore provided a process for treating a mixture of R,R- and S,S-lactide characterised by the steps of:
(a) contacting the mixture of R,R- and S,S-lactide with an aliphatic alcohol and/or an alkoxide to produce a mixture of R,R- and S,S-aliphatic ester of lactyllactic acid;
(b) subsequently contacting the mixture of R,R- and S,S-aliphatic ester of lactyllactic acid with aliphatic alcohol and an enzyme to produce a mixture comprising aliphatic ester of lactic acid corresponding to one lactide enantiomer, and aliphatic ester of lactyllactic acid corresponding to the other lactide enantiomer; and (c) recovering aliphatic ester of lactic acid and/or aliphatic ester of lactyllactic acid from the mixture produced in step (b).

The process of the invention provides lactic acid derivatives in high enantiomeric purity. Preferably, the aliphatic ester of lactic acid obtained from step (c) has an enantiomeric excess of at least 90%, more preferably at least 95%, still more preferably at least 98%, yet more preferably at least 99%. Preferably, the aliphatic ester of lactyllactic acid obtained from step (c) has an enantiomeric excess of at least 90%, more preferably at least 95%, still more preferably at least 98%, still more preferably at least 99%.

Step (a) of the process of the present invention comprises contacting the mixture of R,R- and S,S-lactide with an aliphatic alcohol or an alkoxide to produce a mixture of R,R- and S,S-aliphatic ester of lactyllactic acid. The mixture of R,R- and S,S-lactide may be racemic or scalemic. In one embodiment, the mixture of R,R- and S,S-lactide is racemic. In another embodiment, the mixture of R,R- and S,S-lactide is scalemic (i.e. non racemic). The lactide used in this stage can in principle be derived from any source but one which is particularly suitable is racemic lactic acid produced by treating a monosaccharide (including glucose, fructose, xylose, and mixtures thereof) or a number of other carbohydrates (including formaldehyde, glyceraldehdye, dihydroxyacetone and glycerol) with a base in aqueous solution at elevated temperature. Especially preferred is the use of a Group IA, Group IIA or quaternary ammonium bases as described for example in GB2484674, the prior art discussed therein, and in U.S. Pat. No. 7,829,740. Typically the racemic lactic acid produced in these processes can be converted into racemic lactide by dehydration processes well-known in the art. It is preferred that the lactide is free or substantially free of the corresponding R,S diastereomer (meso lactide). If desired, R,S-lactide may be separated from R,R- and S,S-lactide, for example by routine methods well known in the art.

Suitably the aliphatic alcohol is a $C_1$ to $C_8$ alcohol, preferably a $C_2$ to $C_8$ alcohol, more preferably a $C_3$ to $C_8$ alcohol, most preferably a $C_3$ to $C_4$ alcohol. The aliphatic alcohol is preferably an alkyl alcohol, more preferably a $C_2$ to $C_8$ alkyl alcohol, still more preferably a $C_3$ to $C_8$ alkyl alcohol, yet more preferably a $C_3$ to $C_4$ alkyl alcohol. The alcohol may for example be ethanol, n-propanol, i-propanol, n-butanol, s-butanol, i-butanol or 2-ethylhexanol. Examples of preferred alcohols include ethanol, n-propanol, i-propanol, and n-butanol. More preferably the alcohol is i-propanol, n-propanol or n-butanol. Still more preferably the alcohol is n-propanol or n-butanol. In one particularly preferred embodiment the alkyl alcohol is n-butanol. In another embodiment the aliphatic alcohol is i-propanol. In another embodiment the aliphatic alcohol is n-propanol.

Step (a) can be carried out using the aliphatic alcohol as solvent in which case it is preferred that it is chosen so that the mixture of R,R- and S,S-lactide is completely or partially miscible therewith. Thus, in one embodiment step (a) is carried out in the substantial absence of solvent other than aliphatic alcohol (i.e. in that case the alcohol, lactide and/or enzyme may contain some residual solvent, such as water). In other embodiments, other solvent may be present in addition to the aliphatic alcohol (e.g. a co-solvent) in step (a), for example a solvent/co-solvent that is miscible with the aliphatic alcohol. If the mixture of R,R- and S,S-lactide is immiscible or has only low miscibility with the alcohol it is possible and in many cases preferred to employ a solvent/co-solvent with which both components are miscible. Use of a solvent/co-solvent may also lead to further processing advantages in step (c). Typical preferred examples of solvent/co-solvent include unreactive oxygen-containing solvents for example dialkyl ethers (e.g. diethyl ether, dipropyl ether or MTBE), tetrahydrofuran, 1,4-dioxane, glycol ethers polyalkylene glycol ethers and the like. Ketone solvents/co-solvents are particularly preferred. Preferred ketone solvents include methyl ethyl ketone, methyl isobutyl ketone and, in particular, acetone. Such ketone solvents are particularly suitable for use in processes carried out on an industrial scale, where good solubility properties may be advantageous. Additional hydrocarbon solvents/co-solvents can also be advantageously added. The aliphatic alcohol or the aliphatic alcohol/co-solvent mixture may contain some water. Typically, the aliphatic alcohol or the aliphatic alcohol/co-solvent mixture employed contains less than 1% preferably less than 0.5% by weight water to ensure that the enzyme performs optimally in step (b). In some preferred embodiments, molecular sieves are used in the process.

The process may be conducted using excess aliphatic alcohol together with additional solvent/co-solvent. It will be understood that the process may also be carried out using stoicheometric or even sub-stoicheometric quantities of aliphatic alcohol, and the "other" solvent may be the principal or only solvent.

Step (a), which essentially comprises the ring-opening of the lactide by alcoholysis, can be effected, for example, by heating the mixture of R,R- and S,S-lactide in the presence of the aliphatic alcohol or by the sole or additional use of an alkoxide, preferably the corresponding alkoxide which exhibits strong nucleophilic behaviour towards the racemic lactide. In some embodiments step (a) is carried out in the absence of a catalyst. Alternatively or additionally, step (a) can be carried out in the presence of catalytic amounts of a strong acid such hydrochloric acid, p-toluenesulphonic acid and the like. In all cases the conditions of this step should be carefully monitored to avoid further alcoholysis of the aliphatic lactyllactate ester product to aliphatic lactate ester. For this reason it may be preferred to operate step (a) to less than full conversion, yielding a mixture of alkyl lactyllactate (major component) and unconsumed lactide (minor component), as a suitable feedstock for step (b). Preferably, step (a) is run until 60-90% of the mixture of R,R- and S,S-lactide has been consumed, more preferably until 70-85% of the mixture of R,R- and S,S-lactide has been consumed. The reaction itself is suitably carried out at a temperature in the range of 15 to 140° C., preferably 50 to 120° C. Step (a) is typically carried out in the absence of enzyme. After step (a) has been carried out it is preferred that the product mixture is neutralised, for example by the addition of base where the reaction is acid-catalysed. Typically the amount of aliphatic alcohol used in step (a) is such that the molar ratio of aliphatic alcohol to lactide is in the range 0.5:1 to 10:1, more preferably 0.5:1 to 5:1, still more preferably 0.5:1 to 4:1, yet more preferably 0.5:1 to 3:1, still more preferably 0.5:1 to 2:1, most preferably 0.75:1 to 1.5:1.

In step (b) the mixture of R,R- and S,S-aliphatic ester of lactyllactic acid so 15. produced is contacted with an enzyme and further aliphatic alcohol if required. For example, the enzyme may be added to the reaction product from step (a), or the reaction product from step (a) may be added to the enzyme. The enzyme suitably comprises an esterase which is able to stereoselectively catalyse the reaction of aliphatic ester of lactyllactic acid with aliphatic alcohol to produce aliphatic ester of lactic acid. More preferably, the esterase is a lipase. Preferably the enzyme (e.g. the esterase, lipase) is one which is either chemically or physically immobilised on a porous support for example a polymer resin bead or a silica, alumina or aluminosilicate bead. One particularly preferred example is Lipase B especially *Candida antarctica* Lipase B, a serine hydrolase with known enantiomeric selectivity towards the hydrolysis of secondary alcohol esters. In this aspect of the invention, the Lipase B is most preferably chemically or physically bound to micro or nano beads made of a polymer resin for example a functionalised styrene/divinylbenzene copolymer or a polyacrylate resin as is the case, for example, in the commercially available material Novozym 435 as used in the disclosure by Jeon et al. As Jeon demonstrates, when this particular supported enzyme is used, the aliphatic lactate ester enantiomer that is preferentially produced is that derived from D-lactic acid, and the remaining aliphatic lactyllactate ester enantiomer is that derived from L-lactic acid. Other preferred enzymes include IMMCALB-T2-150, an immobilised lipase B from *Candida antarctica* covalently attached to dry acrylic beads, manufactured by Chiralvision; IMMCALBY-T2-150, a generic lipase B from *Candida antarctica* covalently attached to dry acrylic beads manufactured by Chiralvision; IMMCALB-T1-350, a lipase B from *Candida antarctica* absorbed on dry polypropylene beads, manufactured by Chiralvision; cross-linked aggregate of lipase B from *Candida Antarctica*, manufactured by CLEA; and recombinant *Candida antarctica* lipase B from *Aspergillus oryzae*, supplied by Sigma Aldrich (non-immobilised).

Step (b) can be carried out using the aliphatic alcohol as solvent in which case it is preferred that it is chosen so that the mixture of R,R- and S,S-lactide is completely or partially miscible therewith. Thus, in one embodiment step (b) is carried out in the substantial absence of solvent other than aliphatic alcohol. In other embodiments, a solvent/co-solvent may be employed in step (b), for example a solvent/co-solvent such as those listed above for use in step (a). Ketone solvents such as acetone, methyl ethyl ketone and methyl isobutyl ketone, are again particularly preferred.

Step (b) is suitably carried out at a temperature in the range of from 15 to 140° C. in order to ensure that reaction rates are significant on the one hand and that the enzyme does not deteriorate with long term use on the other. Preferably the temperature employed is in the range 25 to 80° C. most preferably 30 to 70° C.

Typically, when an enzyme such as a *Candida antarctica* lipase B (e.g. Novozym 435) is used, the aliphatic ester of lactic acid and the aliphatic ester of lactyllactic acid are respectively an aliphatic ester of R-lactic acid and an aliphatic ester of S,S-lactyllactic acid. By varying the reaction conditions it may be possible to alter the enzyme selectivity. Thus in another, less preferred, embodiment the enzyme is a *Candida antarctica* lipase B, and the aliphatic ester of lactic acid and the aliphatic ester of lactyllactic acid are respectively an aliphatic ester of S-lactic acid and an aliphatic ester of R,R-lactyllactic acid.

Steps (a) and (b) can be carried out on an industrial scale in a number of ways. For example, if a supported enzyme is used they can be carried out batchwise in a single stirred or highly back-mixed tank where the supported enzyme is added after step (a) and when any neutralisation is complete. Once step (b) is complete the supported enzyme is then separated by filtration or the use of hydrocyclones and the purified liquid fed to, for example, the kettle of a distillation column where step (c) is carried out. In such a case the total residence time in the stirred tank for steps (a) and (b) will typically be in the range up to 24 preferably up to 10, more preferably from 1 to 8 hours and the amount of supported enzyme used will be in the range up to 10% preferably up to 5% by weight of the racemic lactide used.

In an alternative preferred embodiment, a mixture containing, e.g. R,R-butyl lactyllactate and S,S-butyl lactyllactate, alkyl alcohol (e.g. n-butanol) and solvent/co-solvent (e.g. acetone), may be brought into contact with the enzyme (e.g. an immobilised enzyme such as Novozym 435) by passing the mixture through a packed bed of enzyme (e.g. present in a column). In such flow processes, the residency time is selected so as to ensure high conversion. In a particularly preferred embodiment, the packed bed is vertical, and the mixture is fed into the top of the column. Ketone solvents are particularly preferred for use with such processes.

In one preferred embodiment, step (a) is carried out in a continuously operated stirred or back-mixed tank reactor and step (b) is carried out in a downstream tower reactor connected thereto. The two reactors can be operated by for example continuously trickling the liquid product of step (a) down through a fixed or fluidised bed of the supported enzyme contained therein. A product mixture comprising aliphatic ester of lactic acid, aliphatic ester of lactyllactic acid and optionally unreacted lactide, unreacted alcohol and solvent/co-solvent can then be recovered from the bottom of the tower and fed to stage (c). In this arrangement, the contact time of the reactants with the bed is typically in the range of up to 24 hours. Preferably residency times (contact time of the reactants with the bed) are in the range of from 10 minutes to 4 hours, more preferably from 10 minutes to 2 hours. Arrangements of this type permit continuous or semi-continuous generation of product by flow operations. In step (c), the aliphatic ester of lactic acid and/or the aliphatic ester of lactyllactic acid are recovered. Preferably, enzyme is separated from the reaction product obtained from step (b) (e.g. by filtration or decanting), before further treatment to recover aliphatic ester of lactic acid and/or aliphatic ester of lactyllactic acid, facilitating the recovery and re-use (i.e. recycling) of the enzyme. Where the process is operated in a batch-type reactor, the enzyme may for example be separated from the mixture containing aliphatic ester of lactic acid and aliphatic ester of lactyllactic acid by filtration of the enzyme, or by decanting or siphoning off liquid mixture, prior to distillation. Preferably, in the case of a batch-type process, the enzyme is re-used at least once, more preferably at least twice, still more preferably at least 5 times, yet more preferably at least 10 times, most preferably at least 20 times.

In the case of a continuous process where aliphatic ester of lactyllactic acid and alcohol are passed through a packed bed of enzyme (i.e. a continuous or semi-continuous flow process), product and enzyme are continually being separated from one another and the enzyme is continually being recycled. Preferably aliphatic ester of lactic acid and/or aliphatic ester of lactyllactic acid are recovered by distillation, more preferably by distillation under reduced pressure. For example, aliphatic ester of lactic acid (e.g. n-butyl lactate, i-propyl lactate, n-propyl lactate) may be separated from aliphatic ester of lactyllactic acid (e.g. n-butyl lactyllactate, i-propyl lactyllactate, n-propyl lactyllactate) by fractional distillation at a pressure of from 100 Pa (1 mbar) to 10,000 Pa (100 mbar), preferably 1,000 Pa (10 mbar) to 5,000 Pa (50 mbar), more preferably at a pressure of from 2,000 Pa (20 mbar) to 4,000 Pa (40 mbar), and at a temperature of from 40° C. to 170° C., preferably 50° C. to 120° C., more preferably at a temperature of from 75° C. to 110° C.

In that case, at least the lower boiling aliphatic lactate ester fraction is removed overhead for further use or treatment, thereby indirectly effecting separation of the two lactic acid enantiomers. In a preferred embodiment, the aliphatic ester of lactic acid is removed overhead by distillation, and the distillation residue comprises the aliphatic ester of lactyllactic acid, which may be removed via a side stream. In an alternative embodiment, both the aliphatic ester of lactic acid and the aliphatic ester of lactyllactic acid are removed overhead by distillation (e.g. they are collected as separate overhead product streams, for example at different temperatures and/or pressures).

The distillation column (also known as a fractionating column) used must have the necessary number of theoretical plates to perform its function (i.e. to enable separation of aliphatic ester of lactic acid form aliphatic ester of lactyllactic acid). In the case where the reaction is carried out batchwise the reaction will likely have gone to completion and the residuum in the boiler of the distillation column will generally comprise an aliphatic lactyllactate ester fraction which can then be removed by a side stream for its own further treatment and use. If steps (a) and (b) are operated continuously then the distillation column in step (c) will also operate continuously with recycle to either step (a) or (b) to ensure that at steady state the aliphatic ester of R- or S-lactic acid and/or the aliphatic ester of R,R- or S,S-lactyllactic acid can be recovered quantitatively and in optically pure form. In this continuously operated case the distillation can be effected in either a single column or a train of columns arranged in series. Typically the distillation column(s) used in step (c) are operated at a pressure of less than 5,000 Pa.

In an embodiment of the present invention the single enantiomer of the aliphatic lactate ester recovered in step (c) can be converted to either the corresponding lactic acid enantiomer or to the corresponding lactide enantiomer. In both cases, the aliphatic alcohol is released and can be separated and recycled to either step (a) or step (b). For example, in the case where the supported enzyme used is Novozym 435, the alcohol is n-butanol and the solvent is acetone, the R-butyl lactate so generated can be converted to R-lactic acid or R,R-lactide. If R,R-lactide is produced it can then be polymerised to produce optically pure PDLA. Likewise, the single enantiomer of the aliphatic lactyllactate ester if recovered in pure form in step (c) can be converted back to either the corresponding lactic acid or lactide enantiomer so that for example in the case that the aliphatic ester of lactic acid is S,S n-butyl lactyllactate, it can be hydrolysed to S-lactic acid or converted into S,S-lactide, which can then be polymerised to produce optically pure PLLA.

Thus, according to a first further embodiment of the present invention there is provided a process for producing S-lactic acid characterised by the steps of: contacting a mixture of R,R- and S,S-lactide with an aliphatic alcohol and/or alkoxide (e.g. a $C_1$ to $C_8$ alkyl alcohol/alkoxide) to produce a mixture of R,R- and S,S-aliphatic ester of lactyllactic acid; subsequently contacting the mixture of R,R- and S,S-aliphatic ester of lactyllactic acid with aliphatic alcohol and an enzyme to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of S,S-lactyllactic acid, hydrolysing the aliphatic ester of S,S-lactyllactic acid to produce S-lactic acid or, where the aliphatic ester of lactic acid is an aliphatic ester of S-lactic acid, hydrolysing the aliphatic ester of S-lactic acid to produce S-lactic acid. Preferably, the mixture of R,R- and S,S-lactide used in the process is prepared from a mixture of R- and S-lactic acid. The S-lactic acid produced by the process preferably has an enantiomeric excess of at least 90%, more preferably at least 95%, still more preferably at least 98%, most preferably at least 99%.

Alternatively, according to a second further embodiment of the present invention there is provided a process for producing R,R-lactide characterised by the steps of contacting a mixture of R,R- and S,S-lactide with an aliphatic alcohol and/or alkoxide (e.g. a $C_1$ to $C_8$ alkyl alcohol/alkoxide) to produce a mixture of R,R- and S,S-aliphatic ester of lactyllactic acid; subsequently contacting the mixture of R,R- and S,S-aliphatic ester of lactyllactic acid with aliphatic alcohol and an enzyme to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of R,R-lactyllactic acid, converting the aliphatic ester of R,R-lactyllactic acid to R,R-lactide or, where the aliphatic ester of lactic acid is an aliphatic ester of R-lactic acid, converting the aliphatic ester of R-lactic acid to R,R-lactide. Preferably, the mixture of R,R- and S,S-lactide used in the process has been prepared from a mixture of R- and S-lactic acid. The R,R-lactide produced by the process preferably has an enantiomeric excess of at least 90%, more preferably at least 95%, still more preferably at least 98%, most preferably at least 99%.

Alternatively in a third further embodiment of the present invention there is provided a process for producing R-lactic acid characterised by the steps of: contacting a mixture of R,R- and S,S-lactide with an aliphatic alcohol and/or alkoxide (e.g. a $C_1$ to $C_8$ alkyl alcohol/alkoxide) to produce a mixture of R,R- and S,S-aliphatic ester of lactyllactic acid; subsequently contacting the mixture of R,R- and S,S-aliphatic ester of lactyllactic acid with aliphatic alcohol and an enzyme to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of R,R-lactyllactic acid, hydrolysing the aliphatic ester of R,R-lactyllactic acid to produce R-lactic acid or, where the aliphatic ester of lactic acid is an aliphatic ester of R-lactic acid, hydrolysing the aliphatic ester of R-lactic acid to produce R-lactic acid. Preferably, the mixture of R,R- and S,S-lactide used in the process has been prepared from a mixture of R- and S-lactic acid. The R-lactic acid produced by the process preferably has an enantiomeric excess of at least 90%, more preferably at least 95%, still more preferably at least 98%, most preferably at least 99%.

Finally there is provided a process for producing S,S-lactide characterised by the steps of contacting a mixture of R,R- and S,S-lactide with an aliphatic alcohol and/or alkoxide (e.g. a $C_1$ to $C_8$ alkyl alcohol/alkoxide) to produce a mixture of R,R- and S,S-aliphatic ester of lactyllactic acid; subsequently contacting the mixture of R,R- and S,S-aliphatic ester of lactyllactic acid with aliphatic alcohol and an enzyme to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of S,S-lactyllactic acid, converting the aliphatic ester of S,S-lactyllactic acid to S,S-lactide or, where the aliphatic ester of lactic acid is an aliphatic ester of S-lactic acid, converting the aliphatic ester of S-lactic acid to S,S-lactide. Preferably, the mixture of R,R- and S,S-lactide used in the process has been prepared from a mixture of R- and S-lactic acid. The S,S-lactide produced by the process preferably has an enantiomeric excess of at least 90%, more preferably at least 95%, still more preferably at least 98%, most preferably at least 99%.

Conversion of the mixture of R- and S-lactic acid into a mixture of R,R and S,S-lactide may result in formation of R,S-lactide, as well as R,R- and S,S-lactide. If desired, R,S-lactide may be separated from R,R- and S,S-lactide by routine methods well known in the art.

Preferably the R,R- and S,S-lactides produced in respectively the second or fourth further embodiments set out above are separately polymerised to produce substantially optically pure PDLA or PLLA. PDLA and PLLA can be combined in varying proportions, for example using melt blending, to produce a range of stereocomplex polylactic acid formulations having an associated range of improved optical and form stability properties relative to either PLLA or PDLA alone. Whilst the relative proportions of these two polymers can vary widely it is preferred that the PLLA content of these formulations lie in the range 40 to 60% based on the total weight of PLLA and PDLA. The stereocomplex polymers so produced can used in a wide range of applications, including a wider scope of durable uses previously not possible with PLLA.

The invention will now be illustrated by reference to the following examples.

EXAMPLES 1-3

Stereoselective Alcoholysis of Rac-Lactide in Heptane/THF (Batch)

A glass reactor was charged with racemic lactide (1 equivalent), n-butanol (1.5 equivalents), Novozym 435 (3% by weight of the racemic lactide) and varying amounts of a 90:10 (by weight) heptane/THF co-solvent (volumes based on the amount of n-butanol used). The mixture was stirred for 24 hours at room temperature and then analysed by $^1$H NMR spectroscopy and chiral HPLC for R-butyl lactate, S-butyl lactate, S,S-butyl lactyllactate and R,R butyl lactyllactate so that the composition of the lactate components could be determined. The results are shown in the following table (Nd=not detected):

| Example No. | Volume of heptanes/THF | % D-butyl lactate | % L-butyl lactate | % S,S-butyl lactyl-lactate | % R,R-butyl lactyl-lactate |
|---|---|---|---|---|---|
| 1 | 0 | 28 | Nd | 15 | 57 |
| 2 | 3.5 | 26 | Nd | 20 | 54 |
| 3 | 1.0 | 26 | Nd | 19 | 55 |

Examples 1 to 3 are for comparative purposes.

EXAMPLES 4-12

Conversion of Rac-Lactide to Butyl Lactyllactate Using pTSA Acid Catalyst

In these examples the ring opening of racemic lactide was investigated by contacting 1 equivalent of racemic lactide with various equivalents of n-butanol and in the presence (Examples 4 to 7) or absence (Examples 8 to 12) of catalytic amounts (1 mole percent) of p-toluenesulphonic acid in a stirred reactor for various times and at various temperatures.

The results are shown in the following table. Analysis of the products obtained was carried out using $^1$H NMR.

| Example | Temp (° C.) and (time in hrs) | n-butanol equivalents | Lactide (mole %) | Racemic butyl lactyl-lactate (mole %) | Racemic butyl lactate (mole %) |
|---|---|---|---|---|---|
| 4 | 25 (16) | 1.5 | 14 | 78 | 8 |
| 5 | 25 (60) | 1.5 | 0 | 71 | 29 |
| 6 | 100 (3) | 1.0 | 0 | 88 | 12 |
| 7 | 105 (1) | 1.5 | 0 | 64 | 36 |
| 8 | 120 (2) | 1.5 | 81 | 19 | 0 |
| 9 | 120 (4) | 1.5 | 63 | 37 | 0 |
| 10 | 120 (20) | 1.5 | 9 | 86 | 5 |
| 11 | 120 (26) | 1.5 | 4 | 89 | 7 |
| 12 | 140 (4) | 1.5 | Trace | 87 | 13 |

EXAMPLE 13

Uncatalysed Conversion of Rac-Lactide to Rac-Butyl Lactyllactate in Butanol

In a typical process, a 2 L glass reactor (Radley's Reactor Ready range) was charged with 500.8 g rac-lactide (Sigma) and 772.0 g n-butanol (Sigma). The slurry was stirred using an overhead stirrer and heated via an oil-filled jacket to reflux (ca. 120° C.). The reaction was maintained at reflux for between 20 and 50 hrs or until the rac-lactide has been consumed as judged by $^1$H NMR spectroscopy.

By way of example, $^1$H NMR analysis of a reaction solution obtained after 28 hr revealed the mixture composition to be 67.2% butyl lactyl lactate, 2.5% butyl lactate and 30.3% consumed lactide. NMR analysis of a reaction solution obtained after 42 hr revealed the mixture composition to be 85.8% butyl lactyl lactate, 13.4% butyl lactate and 0.8% lactide.

The mixture was then allowed to cool to ambient and transferred to a rotary evaporator. Excess butanol was removed at 20-30 mbar using a water bath set between 70 and 80° C.

The liquid residue was then decanted into a 1 Litre round bottom flask equipped with a short packed column and it was distilled under vacuum. The first major fraction collected between 20-92° C. at 1.4 mbar and consisted of rac-butyl lactate and trace quantities of rac-butyl lactyl lactate. The packed column was then removed and the main product distilled—rac-butyl lactyl lactate collected at 92-95° C. at 1.4 mbar, in typical (unoptimised) yields of 75-90%. Alternatively the rac-butyl lactyl lactate may be distilled at 30 mbar, in which case it collects at 158-162° C.

EXAMPLE 14

Uncatalysed Conversion of Rac-Lactide to Rac-Butyl Lactyl Lactate in Butanol (ca. 40 L Scale)

To a clean, dry 60 L reactor (thick walled QVF borosilicate glass) set up for reflux under atmospheric pressure was charged n-butanol (15.0 kg, 18.5 L). The vessel was then purged with nitrogen and the contents heated to 75-80° C. Solid S,S-lactide (7.830 kg, 54.326 mol) then solid R,R-lactide (7.830 kg, 54.326 mol) were quickly charged into the resulting solution, resulting in a white slurry. Further n-butanol (1.2 kg, 1.5 L) was then used as a rinse, taking the total n-butanol charge to 16.2 kg, 20 L, 218.6 mol.

The vessel was again purged with nitrogen and heated to reflux. All solids dissolved when the internal temperature exceeded 89° C., and reflux was initially established at 113° C., but this temperature slowly increased as the reaction progressed. After 17.5 hours at reflux, the internal temperature had increased to 127° C. and a sample was removed for GC analysis giving the following results:

| Analyte concentration (%). Corrected for dilution. | | | | | | |
|---|---|---|---|---|---|---|
| Butanol | R-butyl lactate | S-butyl lactate | R,R-butyl lactyl lactate | S,S-butyl lactyl lactate | R,R-lactide | S,S-lactide |
| 30.12 | 0.98 | 0.99 | 31.00 | 31.05 | 2.93 | 2.94 |

The mixture was then cooled back to room temperature. Total time above 120° C. had been 19 hours. The resulting mixture then gave the following GC analysis.

| Analyte concentration (%). Corrected for dilution. | | | | | | |
|---|---|---|---|---|---|---|
| Butanol | R-butyl lactate | S-butyl lactate | R,R-butyl lactyl lactate | S,S-butyl lactyl lactate | R,R-lactide | S,S-lactide |
| 26.06 | 1.15 | 1.15 | 33.26 | 33.33 | 2.57 | 2.48 |

Product solution weight obtained=30.64 kg (96.2% of the theoretical 31.86 kg expected).

EXAMPLES 15-17

Stereoselective Alcoholysis of Rac-Butyl Lactyllactate in a Heptane/THF Mixture (Batch)

A glass reactor was charged with a racemic mixture of R,R- and S,S-butyl lactyllactate (1 equivalent), n-butanol (1.5 equivalents), Novozym 435 (3% by weight of the racemic butyl lactyllactate) and varying amounts of a 90:10 (by weight) heptane/THF co-solvent (volumes based on the amount of n-butanol used). The mixture was stirred for 24 hours at room temperature and then analysed by $^1$H NMR spectroscopy and chiral liquid chromatography for R-butyl lactate, S-butyl lactate, S,S-butyl lactyllactate and R,R butyl lactyllactate so that the composition of the lactate components could be determined. The results are shown in the following table:

| Example No. | Volume of heptane/THF co-solvent | % R-butyl lactate | % S-butyl lactate | % S,S-butyl lactyl-lactate | % R,R-butyl lactyl-lactate |
|---|---|---|---|---|---|
| 15 | 0 | 43 | 0 | 7 | 50 |
| 16 | 3.5 | 42 | 0 | 6 | 52 |
| 17 | 1.0 | 43 | 0 | 8 | 49 |

When the results of examples 15 to 17 are compared with the yields obtained in examples 1 to 3 above the improvement in the enzyme conversion process caused by the use of an alkyl lactyllactate, as opposed to a lactide feedstock can be seen.

EXAMPLE 18

Analogous experiments to those described in Examples 15 to 17 were carried out using IMMCALB-T2-150, IMMCALBY-T2-150, IMMCALB-T1-350, a cross-linked aggregate of lipase B from *Candida Antarctica*, or recombinant *Candida antarctica* lipase B from *Aspergillus oryzae*, as the enzyme in place of Novozym 435. Those enzymes showed similar levels of stereoselectivity to Novozym 435.

EXAMPLES 19-21

Stereoselective Alcoholysis of Rac-Butyl Lactyllactate in Butanol/Solvent Mixtures and Recycle of Enzyme (Batch)

Racemic butyl lactyl lactate (1.58 g), n-butanol (3.0 molar equivalents), Novozym 435 (3% wt of butyl lactyl lactate, 0.047 g) and 4.8 ml of tert-butanol, acetone or acetonitrile were stirred in a parallel synthesis block set at 35° C.

After 20h each reaction was stopped and analysed for conversion to R-butyl lactate. The reaction liquors were then carefully separated from the immobilised enzyme by syringe and the enzyme was washed with the respective solvent and reused in a subsequent run. The enzyme was reused for 10 repeat runs during which the conversion to R-butyl lactate was maintained at 80-98% for acetone, heptane and toluene. After the final run chiral liquid chromatography analysis confirmed the R-butyl lactate product was >99% e.e.

Conversions after the $1^{st}$ and $10^{th}$ runs were as follows (determined by NMR and chiral liquid chromatography):

| Example | Solvent | Run 1 conversion (%) | Run 10 conversion (%) |
|---|---|---|---|
| 19 | Acetone | 95 | 81 |
| 20 | tBuOH | 95 | 59 |
| 21 | Acetonitrile | 93 | 50 |

The invention claimed is:

1. A process for producing an aliphatic ester of lactic acid and an aliphatic ester of lactyllactic acid, one of said esters being in the R form and the other being in the S form, characterised by the steps of:
    (a) contacting a mixture of R,R- and S,S-lactide with an aliphatic alcohol and/or an alkoxide to produce a mixture of R,R- and S,S-aliphatic ester of lactyllactic acid;
    (b) subsequently contacting the mixture of R,R- and S,S-aliphatic ester of lactyllactic acid with aliphatic alcohol and an enzyme to produce a mixture comprising aliphatic ester of lactic acid corresponding to one lactide enantiomer (R or S), and the aliphatic ester of lactyllactic acid corresponding to the other lactide enantiomer (S or R); and
    (c) recovering aliphatic ester of lactic acid and/or aliphatic ester of lactyllactic acid from the mixture produced in step (b).

2. The process as claimed in claim 1, wherein the recovered aliphatic ester of lactic acid and/or aliphatic ester of lactyllactic acid has an enantiomeric excess of at least 90%.

3. The process as claimed in claim 1, wherein a solvent which is miscible with the aliphatic alcohol is employed in step (a) and/or step (b).

4. The process as claimed in claim 1, wherein a $C_2$ to $C_8$ aliphatic alcohol is used in step (a) and/or step (b).

5. The process as claimed in claim 4, wherein n-butanol is used in step (a) and/or step (b).

6. The process as claimed in claim 1, wherein the molar ratio of $C_1$ to $C_8$ aliphatic alcohol to lactide in step (a) is in the range 0.5:1 to 4:1.

7. The process as claimed in claim 1, wherein the aliphatic ester of lactic acid and lactyllactic acid recovered in step (c) are respectively an aliphatic ester of R-lactic acid and an aliphatic ester of S,S-lactyllactic acid.

8. The process as claimed in claim 1, wherein the enzyme is chemically or physically immobilised on a porous support.

9. The process as claimed in claim 1, which comprises a further step (d) which comprises converting one or both of the aliphatic ester of lactyllactic acid and the aliphatic ester of lactic acid into the corresponding R,R- or S,S-enantiomer of lactide and/or the corresponding R- or S-enantiomer of lactic acid.

10. The process as claimed in claim 1, wherein the mixture of R,R- and S,S-lactide used in step (a) has been prepared from a mixture of R- and S-lactic acid.

11. The process as claimed in claim 10, wherein the mixture of R- and S-lactic acid has been prepared by treating a monosaccharide or glycerol with a base.

12. The process as claimed in claim 1, wherein step (a) is acid catalysed.

13. The process as claimed in claim 1, wherein the process comprises separating the aliphatic ester of lactic acid from the aliphatic ester of lactyllactic acid by fractional distillation; and either, where the aliphatic ester of lactyllactic acid is an aliphatic ester of S,S-lactyllactic acid, hydrolysing the aliphatic ester of S,S-lactyllactic acid to produce S-lactic acid or, where the aliphatic ester of lactic acid is an aliphatic ester of S-lactic acid, hydrolysing the aliphatic ester of S-lactic acid to produce S-lactic acid.

14. The process as claimed in claim 1, wherein the process comprises separating the aliphatic ester of lactic acid from the aliphatic ester of lactyllactic acid by fractional distillation; and either, where the aliphatic ester of lactyllactic acid is an aliphatic ester of R,R-lactyllactic acid, hydrolysing the aliphatic ester of R,R-lactyllactic acid to produce R-lactic acid or, where the aliphatic ester of lactic acid is an aliphatic ester of R-lactic acid, hydrolysing the aliphatic ester of R-lactic acid to produce R-lactic acid.

15. The process as claimed in claim 1, wherein the process comprises separating the aliphatic ester of lactic acid from the aliphatic ester of lactyllactic acid by fractional distillation; and either, where the aliphatic ester of lactyllactic acid is an aliphatic ester of R,R-lactyllactic acid, converting the aliphatic ester of R,R-lactyllactic acid to R,R-lactide or, where the aliphatic ester of lactic acid is an aliphatic ester of R-lactic acid, converting the aliphatic ester of R-lactic acid to R,R-lactide.

16. The process as claimed in claim 15, wherein the R,R-lactide produced is polymerised to produce poly-R-lactic acid.

17. The process as claimed in claim 16, wherien the poly-R-lactic acid produced is melt blended to form stereocomplex polylactic acid.

18. The process as claimed in claim 1, wherein the process comprises separating the aliphatic ester of lactic acid from the aliphatic ester of lactyllactic acid by fractional distillation; and either, where the aliphatic ester of lactyllactic acid is an aliphatic ester of S,S-lactyllactic acid, converting the aliphatic ester of S,S-lactyllactic acid to S,S-lactide or, where the aliphatic ester of lactic acid is an aliphatic ester of S-lactic acid, converting the aliphatic ester of S-lactic acid to S,S-lactide.

19. The process as claimed in claim 18, wherein the S,S-lactide produced is polymerized to produce poly-S-lactic acid.

20. The process as claimed in claim 19, wherein the poly-S-lactic acid produced is melt blended to form stereocomplex polylactic acid.

* * * * *